United States Patent [19]

Sato et al.

[11] Patent Number: 4,839,360

[45] Date of Patent: Jun. 13, 1989

[54] LACTAM DERIVATIVES

[75] Inventors: Yasuhiko Sato, Urawa; Koichiro Yamada, Kawaguchi; Sumihiro Nomura, Omiya; Ryuichi Ishida, Suita; Michio Yamamura, Tondabayashi, all of Japan

[73] Assignee: Tanabe Seiyaku Co., Ltd., Japan

[21] Appl. No.: 123,314

[22] Filed: Nov. 20, 1987

[30] Foreign Application Priority Data

Dec. 3, 1986 [JP] Japan ................... 61-288079

[51] Int. Cl.$^4$ ............... A61K 31/505; A61K 31/445; C07D 401/10; C07D 211/76
[52] U.S. Cl. ..................... 514/252; 514/256; 514/318; 514/327; 514/427; 544/238; 544/335; 544/336; 546/194; 546/208; 546/216; 548/543
[58] Field of Search .............. 544/238, 335, 336; 546/194, 208, 216; 548/543; 514/318, 327, 427, 252, 256

[56] References Cited

PUBLICATIONS

*Journal of Organic Chemistry*, vol. 41, pp. 2878–2881, (1976) by Smith, et al.

Primary Examiner—Robert T. Bond
Attorney, Agent, or Firm—Scully, Scott, Murphy & Presser

[57] ABSTRACT

There is disclosed a lactam derivative of the formula:

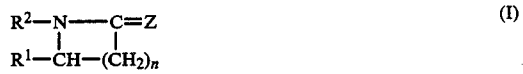

wherein $R^1$ is a substituted or unsubstituted phenyl group; $R^2$ is a substituted or unsubstituted phenyl group, a cycloalkyl group or a nitrogen-containing 6-membered heterocyclic group; Z is oxygen atom or sulfur atom; and n is an integer of 2 or 3, and a salt thereof.

The above lactam derivative is novel and useful as a pharmaceutical compound.

24 Claims, No Drawings

LACTAM DERIVATIVES

SUMMARY OF THE INVENTION

This invention relates to a novel lactam derivative. More particularly, it relates to a lactam derivative of the formula (I)

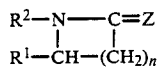

wherein $R^1$ represents a substituted or unsubstituted phenyl group; $R^2$ represents a substituted or unsubstituted phenyl group, a cycloalkyl group or a nitrogen-containing 6-membered heterocyclic group; Z is oxygen atom or sulfur atom; and n is an integer of 2 or 3, or salts thereof.

The compound (I) of the present invention and a salt thereof show potent activating effects on central dopaminergic systems and are useful to improve cerebral functions.

DESCRIPTION OF THE PREFERRED EMBODIMENTS

Examples of the compound of the present invention may include those of the formula (I) in which $R^1$ and/or $R^2$ each represent phenyl group, or a phenyl group having one or two substituent(s) selected from halogen atoms (e.g., fluorine atom, chlorine atom, bromine atom, iodine atom), a lower alkyl group (e.g., methyl group, ethyl group, propyl group, butyl group), hydroxyl group, a lower alkoxy group (e.g., methoxy group, ethoxy group, propoxy group, butoxy group), a lower alkylthio group (e.g., methylthio group, ethylthio group, propylthio group, butylthio group), thiol group, cyano group, a lower alkanoyloxy group (e.g., acetoxy group, propionyloxy group, butyryloxy group, capryloxy group), a lower alkylsulfinyl group (e.g., methanesulfinyl group, ethanesulfinyl group), a lower alkylsulfonyl group (e.g., methanesulfonyl group, ethanesulfonyl group), a trihalo-lower alkyl group (e.g., trifluoromethyl group), nitro group, amino group, a lower alkanoylamino group (e.g., acetylamino group), carboxyl group and a carboxy-lower alkyl group (e.g., carboxymethyl group); or $R^1$ represents a substituted or unsubstituted phenyl group as mentioned above, and $R^2$ represents a cycloalkyl group such as cyclobutyl group, cyclopentyl group, cyclohexyl group and cycloheptyl group, or a nitrogen-containing 6-membered heterocyclic group such as pyridyl group, pyrazinyl group, pyrimidyl group and pyridazinyl group; Z represents oxygen atom or sulfur atom; and n is 2 or 3.

Among the compounds (I) of the present invention, preferred subgenus includes those in which $R^1$ is phenyl group or a phenyl group having one to two substituent(s) selected from a halogen atom, a $C_{1-3}$ alkyl group, a $C_{1-3}$ alkoxy group, a $C_{1-3}$ alkylthio group and hydroxy group; $R^2$ is phenyl group, a phenyl group having one to two substituent(s) selected from a halogen atom, a $C_{1-3}$ alkoxy group, a $C_{1-3}$ alkyl group, a $C_{1-3}$ alkanoylamino group, hydroxy group, nitro group and amino group, or a $C_{4-7}$ cycloalkyl group; Z is oxygen atom; and n is 3.

More preferred subgenus includes those of the formula (I) in which $R^1$ is phenyl group or a phenyl group having 1 to 2 substituent(s) selected from a halogen atom, a $C_{1-3}$ alkyl group and a $C_{1-3}$ alkoxy group; $R^2$ is phenyl group, a phenyl group having one to two substituent(s) selected from a halogen atom, a $C_{1-3}$ alkoxy group, a $C_{1-3}$ alkyl group, nitro group and amino group, or a $C_{4-7}$ cycloalkyl group; Z is oxygen atom; and n is 3.

Still more preferred subgenus includes those of the formula (I) in which $R^1$ is a mono- or di-halogenophenyl group; $R^2$ is phenyl group, or a phenyl group having 1 to 2 substituent(s) selected from a halogen atom, a $C_{1-3}$ alkoxy group, a $C_{1-3}$ alkyl group, nitro group and amino group, or a $C_{4-7}$ cycloalkyl group; Z is oxygen atom; and n is 3.

Most preferred subgenus includes those of the formula (I) in which $R^1$ is a phenyl group having 1 to 2 substituent(s) selected from fluorine atom, chlorine atom, bromine atom or iodine atom; $R^2$ is phenyl group, a phenyl group having a substituent selected from fluorine atom, chlorine atom, methoxy group, methyl group, nitro group and amino group, or cyclohexyl group; Z is oxygen atom; and n is an integer of 3.

While the compound (I) of the present invention may exist in the form of two optical isomers due to the asymmetric carbon atom involved therein, the present invention includes within its scope either one of these isomers and a mixture thereof.

According to the present invention, the compound (I) or a salt thereof can be prepared by (i) intramolecular cyclization of a compound of the formula:

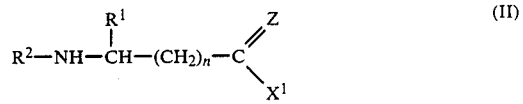

or

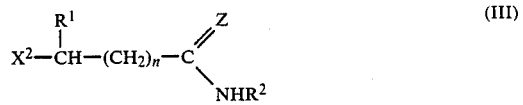

wherein $R^1$, $R^2$, Z and n have the same meanings as defined above, and $X^1$ and $X^2$ represent a reactive residue, or a salt thereof, or (ii) reacting a compound of the formula:

wherein $R^1$, Z and n have the same meanings as defined above, with an amine compound of the formula:

wherein $R^2$ has the same meanings as defined above, or a salt thereof, and (iii) if required, converting the product to a salt thereof.

Alternatively, the compounds (I) in which Z is sulfur atom [hereinafter called Compound (I-A)] or a salt thereof may be prepared by thiocarbonylation of the compounds of the formula (I) in which Z is oxygen atom [hereinafter called Compound (I-B)] or a salt thereof, and if required, further converting the product to a salt thereof.

The compounds (II), (III), (V) and [I-B] may be used for the above-mentioned reactions either in the free form or in the form of a salt thereof. Preferable examples of said salt may include conventional acid addition salts such as hydrochloride, hydrobromide, sulfate, nitrate, methanesulfonate, oxalate, fumarate, maleate, malate, tartarate, citrate, etc.

The intramolecular cyclization of the compound (II) or (III) can be conducted in the presence or absence of a base in an appropriate solvent. Suitable examples of the base include an alkali metal lower alkoxide such as sodium methoxide, potassium methoxide, sodium ethoxide, potassium ethoxide and potassium tert-butoxide, an organic base such as a tri-lower alkylamine (e.g., triethylamine), pyridine, collidine and picoline, an alkali metal hydride such as sodium hydride, an alkali metal amides such as sodium amide, potassium amide, etc. Also, preferable examples of the reactive residues $X^1$ and $X^2$ include a halogen atom wuch as chlorine atom and bromine atom, a lower alkanoyloxy group such as acetoxy group, a substituted or unsubstituted phenylsulfonyloxy group such as tosyloxy group, a lower alkylsulfonyloxy group such as methanesulfonyloxy group, and hydroxyl group, etc. Any inert solvents including, for example, benzene, toluene, xylene, ethyl acetate, methylene chloride, chloroform, dimethylsulfoxide and the like may be used in carrying out the reaction. The above-mentioned reaction may be proceed at $-30°$ C. to $200°$ C., particularly $-10°$ C. to $180°$ C.

The reaction of the compound (IV) and the amine compound (V) or a salt thereof can be accomplished either in the presence or absence of a Lewis acid. The Lewis acid includes, for example, an inorganic acid such as hydrochloric acid, sulfuric acid, p-toluenesulfonic acid, boron trifluoride etherate, zinc chloride, stannous chloride, and the like. Xylene, toluene, benzene, ethyl acetate, methylene chloride, chloroform, dimethylsulfoxide and a lower alkanol are suitable as the solvent. The reaction may proceed at $50°$ C. to $200°$ C., particularly $100°$ C. to $200°$ C.

The thiocarbonylation reaction of the compound (I-B) or a salt thereof can be effected by treatment with a thiocarbonylating agent in an appropriate solvent. Suitable examples of such thiocarbonylating agent include 2,4-bis(4-methoxyphenyl)-1,3-dithia-2,4-diphosphetane-2,4-disulfide, phosphorus pentasulfide, and the like. Dimethoxyethane, pyridine, xylene, toluene, benzene, etc. are suitable as the solvent. The present invention may proceed at $25°$ C. to $150°$ C., particularly $50°$ C. to $100°$ C.

When $R^1$ and/or $R^2$ in the thus-obtained compound (I) is/or are a substituted or unsubstituted phenyl group, substituent(s) may be, if required, introduced onto the phenyl group or the substituent(s) on the phenyl group may be converted to other substituent(s) in conventional manners. For example, the compound (I), in which $R^1$ and/or $R^2$ is a halogeno-phenyl group can be obtained by conventional halogenation of the compound (I) in which $R^1$ and/or $R^2$ is/or are phenyl group. This halogenation may be carried out by treatment of the compound with a halogenating agent. Suitable examples of the halogenating agent include phosphorus pentachloride-sulfuryl chloride, sulfuryl chloride, chlorine in the presence of a catalyst (e.g., iron, ferric chloride, etc). This reaction is preferably carried out in a solvent such as chloroform, methylene chloride, acetic acid at $0°$ to $150°$ C. On the other hand, when $R^1$ and/or $R^2$ is/or are a halogenophenyl group, said compound (I) may be subjected to dehalogenation to give the compound (I) in which $R^1$ and/or $R^2$ is/or are an unsubstituted phenyl group. This dehalogenation may be carried out by catalytic reduction in the presence of a catalyst (e.g., palladium-carbon, palladium-calcium carbonate) in hydrogen gas atmosphere or by treatment with formic acid and/or ammonium formate in the presence of a catalyst (e.g., palladium-carbon). The catalytic hydrogenation may be preferably carried out in an appropriate solvent (methanol, ethanol) at $25°$ to $100°$ C., and the treatment with formic acid and/or ammonium formate may be carried out at $25°$ to $150°$ C. in an appropriate solvent (dimethylformamide, lower alkanols). The compound (I) in which $R^1$ and/or $R^2$ is/or are a halogenophenyl group may be converted to the corresponding cyanophenyl compound by conventional cyanization reaction, the compound (I) in which $R^1$ and/or $R^2$ is/or are a lower alkoxyphenyl group is converted to the corresponding hydroxyphenyl compound by conventional dealkylation thereof, and the compound (I) in which $R^1$ and/or $R^2$ is/or are a lower alkylthiophenyl group may be converted to the corresponding alkylsulfinyl or alkylsulfonyl compound by conventional oxdation thereof. the compound (I) in which $R^1$ and/or $R^2$ is/or are a mercaptophenyl group may be obtained from the compound (I) (in which $R^1$ and/or $R^2$ is/or are a lower alkylsulfonyl group) by treating the latter compound with anhydrous trifluoroacetic acid. Alternatively, the compound (I) in which $R^1$ and/or $R^2$ is/or are phenyl group may be converted to the corresponding nitrophenyl or aminophenyl compound by treating the former compound with nitric aicd, followed by optional reduction thereof. Further, when $R^1$ and/or $R^2$ is/or are an aminophenyl group or a hydroxyphenyl group, said compound may be also converted to the corresponding lower alkanoylaminophenyl or lower alkanoyloxyphenyl compound by conventional acylation thereof.

Since all of the above-mentioned reactions of the present invention proceed without racemization, the compound (I) in an optically active form can be readily obtained by the use of the optically active compounds (II), (III), (IV) or (I-B) as the starting compound.

The compound (I) of the present invention shows potent activating effects on cerebral functions due to the stimulation of central dopaminergic system. More specifically, the compound (I) of the invention can effectively increase the spontaneous locomotor activity, shows potent antagonistic effect on reserpine-induced hypothermia and also shortens the immobility time during forced swimming in mice thereof. For example, when the effect of a test compound on spontaneous locomotor activity was evaluated using Ambulometer for 60 minutes after oral or intraperitoneal administration thereof to male STD/ddy mice, 6-(4-chlorophenyl)-1-phenyl-2-piperidone of the present invention showed a significant increase in the spontaneous locomotor activity at 3 mg/kg or more. Also, when a test compound was administered orally or intraperitoneally to male STD/ddy mice (rectal temp.: not higher than $30°$ C.) 18 to 20 hours after subcutaneous administration or reserpine (30 mg/kg) thereto and the rectal temperature of said mice was measured 30, 60, 120, 180 and 300 minutes after administration of said test compound, 6-(4-chlorophenyl)-1-phenyl-2-piperidone showed the preventive effect against reserpine-induced hypothermia at 10 mg/kg or more. 6-(4-Chlorophenyl)-1-phenyl-2-piperidone when administered orally or intraperitoneally at 1 mg/kg or more also significantly shortened the immobility time of male STD/ddy mice which was subjected to force swimming. Based on these therapeutic effects, the compound (I) of the present invention is useful for therapeutic treatment or amelioration of:

① mental and psychic disorders in senescence (e.g., hypoburia, decreased vital need, hypopsychosis, fatigability, depressive state)
② depression
③ minimal brain dysfunctions in clild (e.g., aprosexia, hyperkinesia, autism), and
④ Parkinson's disease, etc.

Further, the compound (I) of the present invention is useful for treatment of consciousness disorders and amnesia. For example, 6-(4-chlorophenyl)-1-phenyl-2-piperidone at 10 mg/kg or more significantly shortened the recovery time from the loss of righting reflex induced by head blow, and said compound at 1 mg/kg or more also exhibited significant amelioration of retrograde amnesia induced by exposure to pure crbon dioxide gas in the one-trial passive avoidance response in mice. In addition, the compound (I) has high safety for use as a medicine because of no substantial undesirable side effects such as MAO activity inhibiting action, central anticholinergic action, etc.

Among the compound (I) of the present invention, those in which $R^1$ and/or $R^2$ is/or are an aminophenyl group or a lower alkanoylaminophenyl group or $R^2$ is a nitrogen-containing 6-membered heretocyclic group can be used for pharmaceutical use in the form of either the free base or an acid addition salt thereof. Suitable examples of pharmacologically acceptable salt of the compound (I) may include an inorganic acid addition salt such as hydrochloride, hydrobromide, sulfate, an organic acid addition salt such as methansulfonate, oxalate, fumarate, maleate, citrate, malate, tartarate, and the like. These salts can be prepared by, for example, treating the free base of the compound (I) with the stoichiometrically equimolar amount of an acid in a conventional manner.

The compound (I) or a salt thereof can be administered either orally or parenterally, and can be used in association or admixture with pharmaceutical excipients suitable for oral or parenteral administration. Also, pharmaceutical preparations may be solid preparations such as tablets, powders, capsules, or they may be also liquid preparations such as solutions, suspensions and emulsions. Further, when administered parenterally, they can be used in the form of injections.

Among the starting compounds, the compound (II) may be prepared, for example, by (a) reacting compound of the formula:

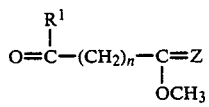
(VI)

wherein $R^1$, Z and n have the same meanings as defined above,
with an amine compound (V) or its salt in a solvent in the presence of a condensing agent (e.g., p-toluenesulfonic acid, treating the product with a reducing agent (e.g., sodium borohydride) to give a compound of the formula:

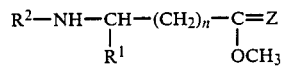
(VII)

wherein $R^1$, $R^2$, Z and n have the same meanings as defined above,
and subsequently hydrolyzing said compound, or (b) treating the compound (VI) and an amine compound (V) or its salt with a reducing agent (e.g., sodium borohydride) in the presence of a base, and (c) if required, converting the hydroxyl group of the thus-obtained compound [i.e., the compound (II) in which $X^1$=hydroxyl group] to other reactive residues in a conventional manner. Also, the starting compound (IV) may be obtained, for example, by treating a compound of the formula:

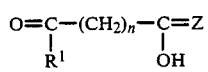
(VIII)

wherein $R^1$, Z and n have the same meanings as defined above,
with a reducing agent (e.g., sodium borohydride) to obtain a compound of the formula:

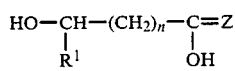
(IX)

wherein $R^1$, Z and n have the same meanings as defined above,
followed by lactonization in the presence of an acid (e.g., inorganic acid, p-toluenesulfonic acid, isobutyl chlorocarbonate, etc.). The starting compound (III) may be obtained, for example, by reaction of the commpound (IV) with the amine compound (V) or its salt in the presence or absence of a Lewis acid; or by treating the compound (IX) with a halogenating agent, followed by reaction with the amine compound (V) or its salt in the presence of an organic base (triethylamine, pyridine, etc.).

Concomitantly, the starting compounds of the invvention in racemic form may be, if required, resolved into each optically active isomers thereof. For example, the optical resolution of the starting compound (II) may be carried out by reacting an O-alkyl derivative of the starting compound (II) [X=hydroxyl group] with (S)-1-(2-naphthylsulfonyl)pyrrolidinyl-2-carbonyl chloride, separating the resultant diastereomers by taking advantage of their difference in solubility, or separating these diastereomers by column chromatography, followed by simultaneously hydrolysis and deesterification thereof.

The compound (I-B), (II), (III) or (IV) thus obtained may be isolated and purified prior to the subsequent step(s), or, if required, be used therefore without such isolation and purification.

Throughout the specification and claims, the term "lower alkyl", "lower alkoxy", "lower alkanoyl" and "cycloalkyl" should be interpreted as referring to alkyl groups of one to four carbon atoms, alkoxy groups of one to four carbon atoms, alkanoyl groups of two to five carbon atoms, and cycloalkyl groups of three to seven carbon atoms, respectively.

EXAMPLES

In the following, the present invention will be described in more detail by referring to the Examples.

Example 1

(1)-a) To 19.0 g of methyl 4-(4-chlorobenzoyl)butyrate were added 14.5 g of aniline, 0.6 g of p-toluenesulfonic acid monohydrate and 200 ml of toluene, and the mixture was refluxed with dehydration for 22.5 hours. After removal of the solvent under reduced pressure, 100 ml of methanol and 2.5 g of sodium hydrogencarbonate were added, and the mixture was cooled to −20° C. Subsequently, 6.0 g of sodium borohydride was added portionwise over 1 hour, and the mixture was stirred at −30° to −20° C. for 1 hour and at −20° to −5° C. for 1 hour. The reaction mixture was diluted with water and extracted with ethyl acetate. The ethyl acetate extracts were washed with diluted hydrochloric acid, and aqueous sodium hydrogencarbonate solution and water, and dried, followed by evaporation of the solvent to give 23.7 g of methyl 5-anilino-5-(4-chlorophenyl)pentanoate as a pale brown oily product. Subsequently, to said oily product were added 75 ml of methanol and 100 ml of an aqueous 10% sodium hydroxide solution, and the mixture was heated under reflux for 1 hour. After removal of the solvent, the residue was diluted with 50 ml of water and then ashed with ether. The aqueous layer was adjusted to pH 6 to 7 with hydrochloric acid, extracted with ethyl acetate. The ethyl acetate extract was washed with diluted hydrochloric acid and a saturated aqueous sodium chloride solution, dried, and treated with activated charcoal. After removal of charcoal and the solvent, the residue was recrystallized from isopropyl ether to give 17.8 g of 5-anilino-5-(4-chlorophenyl)pentanoic acid as colorless prisms.

Yield: 76% m.p.: 133° to 134° C.

IR $\nu_{max}^{nujol}$(cm$^{-1}$): 3420, 2760–2400, 1700

Mass (m/e): 303 (M$^+$)

(1)-(b) To 19.0 g of methyl 4-(4-chlorobenzoyl)butyrate was added 14.5 g of aniline, 0.6 g of p-toluenesulfonic acid monohydrate and 200 ml of toluene, and the mixture was refluxed with dehydration for 22.5 hours. The solvent was evaporated off under reduced pressure, and the residue was dissolved in 200 ml of methanol. A solution of 40 ml of an aqueous 20% sodium hydroxide solution and 3.0 g of sodium borohydride were added at 0° C., and the mixture was stirred at −3° to +5° C. for 1 hour. The reaction temperature was raised to room temperature, and then heated at 60° C. for 1 hour. After removal of solvent, the residue was diluted with 60 ml of water, adjusted to pH 6 to 7 with concentrated hydrochloric acid, extracted with ethyl acetate. The ethyl acetate extract was washed with diluted hydrochloric acid and a saturated aqueous sodium chloride solution, dried, and treated with activated charcoal. After removal of charcoal and the solvent, the residue was recrystallized from isopropyl ether to give 18.5 g of 5-anilino-5-(4-chlorophenyl)pentanoic acid as colorless prisms.

Yield: 77.1%

M.p., IR and MS spectra of this product were identical with those of the compound obtained in Example 1-(1)-(a).

(2)-(a) A solution of 17.8 g of 5-anilino-5-(4-chlorophenyl)pentanoic acid in a mixed solution of 290 ml of toluene and 13.9 g of pyridine was cooled to −3° C. and stirred. To this solution was added 10 ml solution of 5.1 ml of thionyl chloride in toluene dropwise over 1 hour. After stirring at −3° C. for 1 hour and at room temperature for 1.5 hours, the reaction mixture was poured into ice-water. The toluene layer was washed with diluted hydrochloric acid, a saturated aqueous sodium chloride solution, a saturated aqueous sodium hydrogencarbonate solution and a saturated aqueous sodium chloride solution, dried and treated with activated charcoal. After removal of charcoal and the solvent, the residual solid was recrystallized from isopropyl ether to give 16.4 g of 6-(4-chlorophenyl)-1-phenyl-2-piperidone as colorless prisms.

Yield: 82% m.p.: 102.5° to 103.5° C.

IR $\nu_{max}^{nujol}$ (cm$^{-1}$): 1640, 1600

Mass (m/e): 285 (M$^+$)

$^1$H-NMR (CDCl$_3$, δ): 1.60–2.53 (4H, m), 2.68 (2H, t-like; J=6.6 Hz), 4.83–5.10 (1H, m), 6.95–7.40 (9H, m)

(2)-(b) To a suspended solution of 2.0 g of 5-anilino-5-(4-chlorophenyl)pentanoic acid in 10 ml of toluene and 520 mg of pyridine was added 1.21 g of acetic anhydride at 25° C., and the solution was stirred at same temperature for 1.5 hours. Then, the reaction solution was treated in the same manner as in Example 1-(2)-(a) to give 1.51 g of 6-(4-chlorophenyl)-1-phenyl-2-piperidone.

Yield: 80.5%

M.p., IR, MS and NMR spectra of this product were identical with those of the compound obtained in paragraph (2)-(a).

Examples 2 to 33

(1) Corresponding starting compounds were treated in the same manner as in Example 1-(1)-(a) to (b) to give the compounds listed below in Table 1.

TABLE 1

$$R^1-\overset{O}{\underset{\|}{C}}-(CH_2)_n-\overset{Z}{\underset{\|}{C}}-OCH_3 \longrightarrow R^2-NH-\overset{R^1}{\underset{|}{CH}}-(CH_2)_n-\overset{Z}{\underset{\|}{C}}OCH_3$$

(VI)  (VII)

$$\longrightarrow R^2-NH-\overset{R^1}{\underset{|}{CH}}-(CH_2)_n-\overset{Z}{\underset{\|}{C}}X^1 \quad (Z = O, n = 3, X^1 = OH)$$

(II)

| Example No. | Compound (II) R¹ | R² | Physical property m.p. (°C.) (solvent for recrystallization) | Yield (%) |
|---|---|---|---|---|
| 2-(1) | 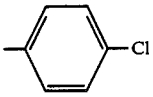 4-Cl-phenyl | 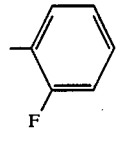 2-F-phenyl | Oily product | 50 |
| 3-(1) | 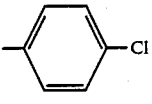 4-Cl-phenyl | 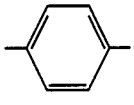 4-Cl-phenyl | 153.5–154.5 n-hexane) | 59 |
| 4-(1) | 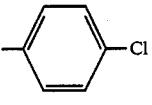 4-Cl-phenyl | 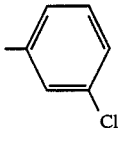 3-Cl-phenyl | Oily product | 66 |
| 5-(1) | 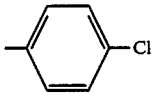 4-Cl-phenyl | 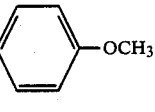 4-OCH₃-phenyl | Oily product | 80 |
| 6-(1) | 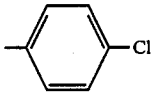 4-Cl-phenyl | 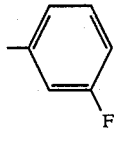 3-F-phenyl | Oily product | 62 |
| 7-(1) | 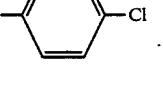 4-Cl-phenyl | 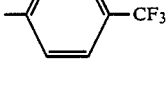 4-CF₃-phenyl | Oily product | — |
| 8-(1) | 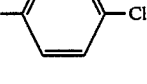 4-Cl-phenyl | 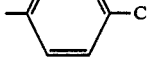 4-CH₃-phenyl | 124–125 (ethyl acetate-n-hexane) | 65 |
| 9-(1) | 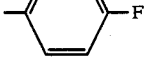 4-F-phenyl | 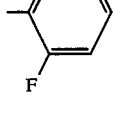 2-F-phenyl | 55–57 (ether-n-hexane) | 56 |
| 10-(1) | 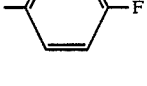 4-F-phenyl | 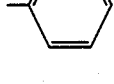 phenyl | 102–104.5 (isopropyl ether) | 48 |
| 11-(1) | 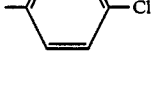 4-Cl-phenyl |  4-I-phenyl | Oily product | — |

TABLE 1-continued $$R^1-\overset{O}{\underset{\|}{C}}-(CH_2)_n-\overset{Z}{\underset{\|}{C}}-OCH_3 \longrightarrow R^2-NH-\overset{R^1}{\underset{|}{CH}}-(CH_2)_n-\overset{Z}{\underset{\|}{C}}OCH_3$$

(VI) (VII)

$$\longrightarrow R^2-NH-\overset{R^1}{\underset{|}{CH}}-(CH_2)_n-\overset{Z}{\underset{\|}{C}}X^1 \quad (Z = O, n = 3, X^1 = OH)$$

(II)

| Example No. | Compound (II) R$^1$ | Compound (II) R$^2$ | Physical property m.p. (°C.) (solvent for recrystallization) | Yield (%) |
|---|---|---|---|---|
| 12-(1) | 4-Cl-C$_6$H$_4$- | cyclohexyl | — | — |
| 13-(1) | 4-Cl-C$_6$H$_4$- | 4-Br-C$_6$H$_4$- | 156.5–158.5 (ethyl acetate-n-hexane) | 79 |
| 14-(1) | 4-Cl-C$_6$H$_4$- | 4-F-C$_6$H$_4$- | 121.5–122 (isopropyl ether-n-hexane) | 95 |
| 15-(1) | 4-Cl-C$_6$H$_4$- | 3-OCH$_3$-C$_6$H$_4$- | Oily product | 84 |
| 16-(1) | 4-I-C$_6$H$_4$- | C$_6$H$_5$- | 131–133 (isopropyl ether) | 82 |
| 17-(1) | 4-Br-C$_6$H$_4$- | C$_6$H$_5$- | 125.5–126 (isopropyl ether-n-hexane) | 81 |
| 18-(1) | 4-CH$_3$-C$_6$H$_4$- | C$_6$H$_5$- | 125.5–126 (isopropyl ether) | 84 |
| 19-(1) | 4-F-C$_6$H$_4$- | 4-F-C$_6$H$_4$- | 106–108 (isopropyl ether) | 76 |
| 20-(1) | 4-SCH$_3$-C$_6$H$_4$- | 4-Cl-C$_6$H$_4$- | Oily product | 93 |
| 21-(1) | 4-OCH$_3$-C$_6$H$_4$- | 4-Cl-C$_6$H$_4$- | Oily product | 54 |
| 22-(1) | 4-SCH$_3$-C$_6$H$_4$- | C$_6$H$_5$- | Oily product | 59 |

TABLE 1-continued $$R^1-\overset{O}{\overset{\|}{C}}-(CH_2)_n-\overset{Z}{\overset{\|}{C}}-OCH_3 \longrightarrow R^2-NH-\overset{R^1}{\overset{|}{CH}}-(CH_2)_n-\overset{Z}{\overset{\|}{C}}OCH_3$$
(VI) \qquad\qquad (VII)

$$\longrightarrow R^2-NH-\overset{R^1}{\overset{|}{CH}}-(CH_2)_n-\overset{Z}{\overset{\|}{C}}X^1 \quad (Z=O, n=3, X^1=OH)$$
(II)

| Example No. | Compound (II) R$^1$ | R$^2$ | Physical property m.p. (°C.) (solvent for recrystallization) | Yield (%) |
|---|---|---|---|---|
| 23-(1) | 4-OCH$_3$-C$_6$H$_4$- | 4-F-C$_6$H$_4$- | Oily product | — |
| 24-(1) | 2-Cl-C$_6$H$_4$- | C$_6$H$_5$- | 120.5–122 (isopropyl ether-n-hexane) | 65 |
| 25-(1) | 3-Cl-C$_6$H$_4$- | C$_6$H$_5$- | Oily product | 67 |
| 26-(1) | 4-Cl-C$_6$H$_4$- | 3,4-Cl$_2$-C$_6$H$_3$- | 140–141.5 (isopropyl | 82 |
| 27-(1) | 4-Cl-C$_6$H$_4$- | 3,5-(CH$_3$)$_2$-C$_6$H$_3$- | Oily product | 85 |
| 28-(1) | 4-Cl-C$_6$H$_4$- | 3,4-(OCH$_3$)$_2$-C$_6$H$_3$- | Oily product | — |
| 29-(1) | 3,4-(OCH$_3$)$_2$-C$_6$H$_3$- | 4-Cl-C$_6$H$_4$- | Oily product | 64 |
| 30-(1) | 3,4-Cl$_2$-C$_6$H$_3$- | C$_6$H$_5$- | 134.5–135.5 (isopropyl ether-ethyl acetate) | 73 |

TABLE 1-continued $$R^1-\overset{O}{\underset{\|}{C}}-(CH_2)_n-\overset{Z}{\underset{\|}{C}}-OCH_3 \longrightarrow R^2-NH-\overset{R^1}{\underset{|}{CH}}-(CH_2)_n-\overset{Z}{\underset{\|}{C}}OCH_3$$

(VI) → (VII)

$$\longrightarrow R^2-NH-\overset{R^1}{\underset{|}{CH}}-(CH_2)_n-\overset{Z}{\underset{\|}{C}}X^1 \quad (Z = O, n = 3, X^1 = OH)$$

(II)

| Example No. | Compound (II) R$^1$ | R$^2$ | Physical property m.p. (°C.) (solvent for recrystallization) | Yield (%) |
|---|---|---|---|---|
| 31-(1) | 3,4-diCl-phenyl | phenyl | Oily product | 78 |
| 32-(1) | 3,4-diCl-phenyl | 4-NO$_2$-phenyl | Caramel | — |
| 33-(1) | 3,4-diCl-phenyl | 3-NO$_2$-phenyl | Caramel | — |

(2) The products (II) obtained above were treated in the same manner as in Example 1-(2)-(a) or -(b) to give the compounds listed below in Table 2.

TABLE 2

$$R^2-NH-\overset{R^1}{\underset{|}{CH}}-(CH_2)_n-\overset{Z}{\underset{\|}{C}}-X^1 \longrightarrow \overset{R^2-N\phantom{xx}C=Z}{\underset{R^1-CH-(CH_2)_n}{|\phantom{xxxxx}|}}$$

(II) → (I)

(Z = O, n = 3, X$^1$ = OH)

| Example No. | Compound (I) R$^1$ | R$^2$ | Physical property m.p. (°C.) for solvent for recrystallization), IR | Yield (%) |
|---|---|---|---|---|
| 2-(2) | 4-Cl-phenyl | 2-F-phenyl | 133–133.5 (ethyl acetate-ether) IR$\nu_{max}^{nujol}$ (cm$^{-1}$):1650 | — |
| 3-(2) | 4-Cl-phenyl | 4-Cl-phenyl | 129–129.5 (isopropyl ether) IR$\nu_{max}^{nujol}$ (cm$^{-1}$):1645 | 87 |
| 4-(2) | 4-Cl-phenyl | 3-Cl-phenyl | Oily product IR$\nu_{max}^{CHCl_3}$ (cm$^{-1}$):1645 | 83 |

TABLE 2-continued $$R^2\text{—NH—}\underset{\underset{R^1}{|}}{CH}\text{—}(CH_2)_n\text{—}\underset{\underset{X^1}{|}}{C}\text{=}Z \longrightarrow \underset{\underset{R^1}{|}}{R^2\text{—N—C=Z}}\text{—CH—}(CH_2)_n$$

(II)        (I)

($Z = O$, $n = 3$, $X^1 = OH$)

| Example No. | Compound (I) R¹ | R² | Physical property m.p. (°C.) for solvent for recrystallization), IR | Yield (%) |
|---|---|---|---|---|
| 5-(2) | 4-Cl-C₆H₄ | 4-OCH₃-C₆H₄ | 129.5–130.0 (ethyl acetate-n-hexane) IR$\nu_{max}^{CHCl_3}$ (cm⁻¹):1640 | 68 |
| 6-(2) | 4-Cl-C₆H₄ | 3-F-C₆H₄ | 90.5–91.5 (isopropyl ether) IR$\nu_{max}^{nujol}$ (cm⁻¹):1640 | 72 |
| 7-(2) | 4-Cl-C₆H₄ | 4-CF₃-C₆H₄ | 95–96 (isopropyl ether-n-hexane) IR$\nu_{max}^{nujol}$ (cm⁻¹):1650 | 79 |
| 8-(2) | 4-Cl-C₆H₄ | 4-CH₃-C₆H₄ | 101.5–103.5 (isopropyl ether) IR$\nu_{max}^{nujol}$ (cm⁻¹):1640 | 84 |
| 9-(2) | 4-F-C₆H₄ | 2-F-C₆H₄ | 101–102.5 (isopropyl ether) IR$\nu_{max}^{nujol}$ (cm⁻¹):1650 | 79 |
| 10-(2) | 4-F-C₆H₄ | C₆H₅ | 82–83 (isopropyl ether) IR$\nu_{max}^{nujol}$ (cm⁻¹):1640 | 70 |
| 11-(2) | 4-Cl-C₆H₄ | 4-I-C₆H₄ | 176–177 (ethyl acetate-isopropyl ether-n-hexane) IR$\nu_{max}^{nujol}$ (cm⁻¹):1645 | — |
| 12-(2) | 4-Cl-C₆H₄ | cyclohexyl | Oily product IR$\nu_{max}^{CHCl_3}$ (cm⁻¹):1620 | — |
| 13-(2) | 4-Cl-C₆H₄ | 4-Br-C₆H₄ | 151.5–152.0 (ethyl acetate-isopropyl ether) IR$\nu_{max}^{nujol}$ (cm⁻¹):1640 | 66 |
| 14-(2) | 4-Cl-C₆H₄ | 4-F-C₆H₄ | 92.5–93.5 (ethyl acetate-n-hexane) IR$\nu_{max}^{nujol}$ (cm⁻¹):1650 | 90 |
| 16-(2) | 4-I-C₆H₄ | C₆H₅ | 137–140 (ether) IR$\nu_{max}^{nujol}$ (cm⁻¹):1640 | 86 |

TABLE 2-continued $$R^2-NH-\underset{\underset{R^1}{|}}{CH}-(CH_2)_n-\underset{\underset{X^1}{|}}{\overset{\overset{Z}{\|}}{C}} \longrightarrow \underset{\underset{R^1-CH-(CH_2)_n}{|}}{\overset{R^2-N-C=Z}{|}}$$

(II)            (I)

(Z = O, n = 3, X$^1$ = OH)

| Example No. | Compound (I) R$^1$ | R$^2$ | Physical property m.p. (°C.) for solvent for recrystallization), IR | Yield (%) |
|---|---|---|---|---|
| 17-(2) | 4-Br-C$_6$H$_4$ | C$_6$H$_5$ | 110–112 (ether) IR$\nu_{max}^{nujol}$ (cm$^{-1}$):1640 | |
| 18-(2) | 4-CH$_3$-C$_6$H$_4$ | C$_6$H$_5$ | 123–124.5 (ethyl acetate-n-hexane) IR$\nu_{max}^{nujol}$ (cm$^{-1}$):1650 | 88 |
| 19-(2) | 4-F-C$_6$H$_4$ | 4-F-C$_6$H$_4$ | 97–98 (isopropyl ether) IR$\nu_{max}^{nujol}$ (cm$^{-1}$):1650 | 72 |
| 20-(2) | 4-SCH$_3$-C$_6$H$_4$ | 4-Cl-C$_6$H$_4$ | 99–100 (isopropyl ether-ethyl acetate) IR$\nu_{max}^{CHCl_3}$ (cm$^{-1}$):1645 | 93 |
| 21-(2) | 4-OCH$_3$-C$_6$H$_4$ | 4-Cl-C$_6$H$_4$ | 104–105 (ethyl acetate-n-hexane) IR$\nu_{max}^{nujol}$ (cm$^{-1}$):1640 | 60 |
| 22-(2) | 4-SCH$_3$-C$_6$H$_4$ | C$_6$H$_5$ | 107–108 (ethyl acetate-isopropyl ether) IR$\nu_{max}^{nujol}$ (cm$^{-1}$):1645 | 64 |
| 23-(2) | 4-OCH$_3$-C$_6$H$_4$ | 4-F-C$_6$H$_4$ | 100–101 (ethyl acetate-isopropyl ether-n-hexane) IR$\nu_{max}^{nujol}$ (cm$^{-1}$):1650 | 80 |
| 24-(2) | 2-Cl-C$_6$H$_4$ | C$_6$H$_5$ | 112–113 (isopropyl ether) IR$\nu_{max}^{nujol}$ (cm$^{-1}$):1650 | 80 |
| 25-(2) | 3-Cl-C$_6$H$_4$ | C$_6$H$_5$ | 70–71 (ethyl acetate-n-hexane) IR$\nu_{max}^{nujol}$ (cm$^{-1}$):1640 | 59 |
| 26-(2) | 4-Cl-C$_6$H$_4$ | 3,4-Cl$_2$-C$_6$H$_3$ | 115–116 (ether-n-hexane) IR$\nu_{max}^{nujol}$ (cm$^{-1}$):1650 | 88 |

TABLE 2-continued $$R^2-NH-\underset{R^1}{\overset{|}{CH}}-(CH_2)_n-\overset{Z}{\underset{|}{C}}-X^1 \longrightarrow \underset{R^1-CH-(CH_2)_n}{\overset{R^2-N——C=Z}{|\qquad\quad|}}$$

(II) → (I)

(Z = O, n = 3, X$^1$ = OH)

| Example No. | Compound (I) R$^1$ | R$^2$ | Physical property m.p. (°C.) for solvent for recrystallization), IR | Yield (%) |
|---|---|---|---|---|
| 27-(2) | 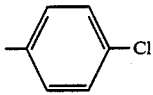 | 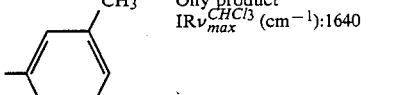 | Oily product IRν$_{max}^{CHCl_3}$ (cm$^{-1}$):1640 | 81 |
| 28-(2) | 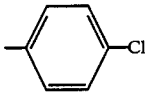 | 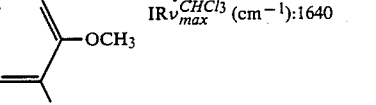 | Oily product IRν$_{max}^{CHCl_3}$ (cm$^{-1}$):1640 | 51 |
| 29-(2) | 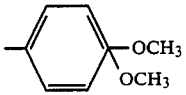 | 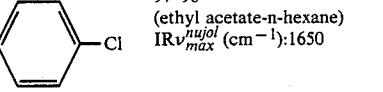 | 97–98 (ethyl acetate-n-hexane) IRν$_{max}^{nujol}$ (cm$^{-1}$):1650 | 77 |
| 30-(2) | 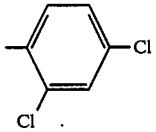 | 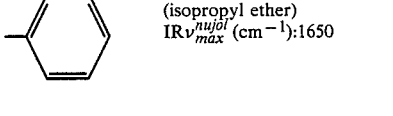 | 109.5–110.5 (isopropyl ether) IRν$_{max}^{nujol}$ (cm$^{-1}$):1650 | 68 |
| 31-(2) | 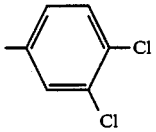 | 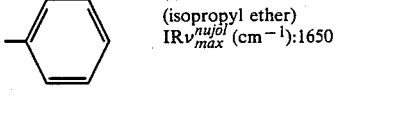 | 88–89 (isopropyl ether) IRν$_{max}^{nujol}$ (cm$^{-1}$):1650 | 59 |
| 32-(2) | 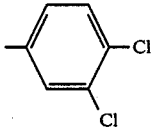 | 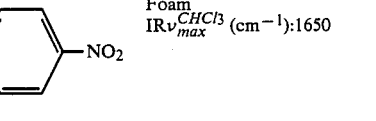 | Foam IRν$_{max}^{CHCl_3}$ (cm$^{-1}$):1650 | 96 |
| 33-(2) | 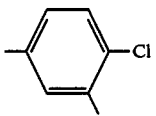 | 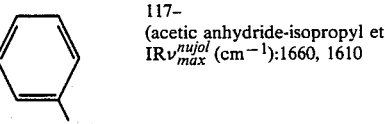 | 117– (acetic anhydride-isopropyl ether) IRν$_{max}^{nujol}$ (cm$^{-1}$):1660, 1610 | |

Example 24

(1) To 35 g of 5-anilino-5-(4-chlorophenyl)pentanoic acid was added 340 ml of 9% methanolic hydrogen chloride solution and the mixture was refluxed for 2.5 hours. After leaving the mixture to stand at room temperature for overnight, the precipitated crystals were filterd and washed with ethyl acetate to give 29 g of methyl 5-anilino-5-(4-chlorophenyl)pentanoate hydrochloride.

Yield: 71.2% m.p.: 188.5° to 190.0° C. (recrystallized from methanol)

(2) To a suspension of 28 g of methyl 5-anilino-5-(4-chlorophenyl)pentanoate hydrochloride in 220 ml of methylene chloride was added, under ice-cooling, a solution of 36.5 g of sodium hydrogencarbonate in 400 ml of water. Subsequently, 41 g of (S)-1-(2-naphthylsulfonyl)pyrrolidinyl-2-carbonyl chloride was added and the mixture was stirred at room temperature for 92 hours. The methylene chloride layer was washed with water, dried and then the solvent was distilled off. The residue was purified by silica gel column chromatography (solvent; ethyl acetate:n-hexane=1:1) to give two kinds of diastereomers of methyl 5-(4-chlorophenyl)-5-

[(S)-1-(2-naphthylsulfonyl)-2-pyrrolidinylanilide] pentanoate (hereinafter called products A and B).

Product A: colorless caramel

Yield: 16.3 g
$[\alpha]_D^{20} -37.9°$ (c=1.0, chloroform)
IR $\nu_{max}^{CHCl_3}$(cm$^{-1}$): 1730, 1660
Mass (m/e): 604 (M$^+$)

Product B: colorless caramel

Yield: 19.9 g
$[\alpha]_D^{20} -8.9°$ (c=1.0, chloroform)
IR $\nu_{max}^{CHCl_3}$(cm$^{-1}$): 1730, 1660
Mass (m/e): 604 (M$^+$)

(3) To a solution of 13.9 g of the product A in 112 ml of 2-ethoxyethanol were added a solution of 30.1 g of 86% potassium hydroxide in 15 ml of water, and the mixture was refluxed at an external temperature of 140° to 150° C. for 2 hours. After cooling, the mixture was adjusted to pH 7 with hydrochloric acid, extracted with ethyl acetate, washed with water and dried, followed by evaporation of the solvent. The residue was purified by silica gel column chromatography (solvent; chloroform:methanol=20:1) to give 5.3 g of (−)-5-anilino-5-(4-chlorophenyl)pentanoic acid as caramel.

Yield: 76%
$[\alpha]_D^{20} -22.2°$ (c=0.54, chloroform)

Methyl ester:

m.p.: 200° to 203° C. (recrystallized from methanol, decomposed)
$[\alpha]_D^{20} -93.7°$ (c=0.51, methanol)

Also, 13.9 g of the product B was treated in the same manner as described above to give 5.3 g of (+)-5-anilino-5-(4-chlorophenyl)pentanoic acid as caramel.

Yield: 76%
$[\alpha]_D^{20} +23.1°$ (c=0.36, chloroform)

Methyl ester:

m.p.: 200° to 203° C. (recrystallized from methanol, decomposed)
$[\alpha]_D^{20} +92.1°$ (c=0.50, methanol)

(4) (−)-5-anilino-5-(4-chlorophenyl)pentanoic acid was treated in the same manner as in Example 1-(2)-(a) to give (−)-(S)-6-(4-chlorophenyl)-1-phenyl-2-piperidone.

Yield: 75%
m.p.: 77.5° to 80.0° C. (recrystallized from a mixture of isopropyl ether-ethyl acetate)
$[\alpha]_D^{20} -164.0°$ (c=0.98, chloroform)

Also, (+)-5-anilino-5-(4-chlorophenyl)pentanoic acid was treated in the same manner as described above to give (+)-(R)-6-(4-chlorophenyl)-1-phenyl-2-piperidone.

Yield: 75%
m.p.: 76.5° to 79.0° C. (recrystallized from a mixture of isopropyl ether-ethyl acetate)
$[\alpha]_D^{20} +166.0°$ (c=1.0, chloroform)

Mass and NMR spectra of the respective isomers were identical with those of the compound obtained in Example 1-(2).

Example 35

To a solution of 7.9 g of methyl 4-chlorobenzoylpropionate in 70 ml of toluene were added 6.3 g of aniline and 0.3 g of p-toluenesulfonic acid, and the mixture was refluxed with dehydration for 24 hours. The solvent was distilled off and the residue was diluted with 100 ml of methanol and 30 ml of an aqueous 10% sodium hydroxide solution, cooled to 0° to 10° C. and 3.7 g of sodium borohydride was added portionwise with stirring. After stirring, at 0° to 10° C. for 1 hour and at room temperature for 30 minutes, the mixture was refluxed for 15 minutes. The solvent was distilled off and the residue was made acidic with diluted hydrochloric acid, extracted with ether, washed with water and dried. After removal of the solvent, the residue was recrystallized from isopropyl ether to give 6.2 g of 5-(4-chlorophenyl)-1-phenyl-2-pyrrolidone.

Yield: 65%
m.p.: 82.5° to 83.5° C.
IR $\nu_{max}^{CHCl_3}$(cm$^{-1}$): 1695
Mass (m/e): 271 (M$^+$)
$^1$H-NMR (CHCl$_3$, δ): 1.8–2.2 (1H, m), 2.4–2.9 (3H, m), 5.15–5.3 (1H, m), 7.0–7.45 (9H, m)

Example 36

(1) To a solution of 10.6 g of 4-(4-chlorobenzoyl)butanoic acid and 1.9 g of sodium hydroxide in 50 ml of water was added under ice-cooling 2.7 g of sodium borohydride portionwise over 35 minutes, and the mixture was stirred at room temperature for 24 hours. The mixture was made acidic with diluted hydrochloric acid under ice-cooling, extracted with ether. The ether extract was washed with water and dried. After removal of the solvent, the residue was recrystallized from a mixture of ethyl acetate-n-hexane to give 7.50 g of 5-(4-chlorophenyl)-5-hydroxypentanoic acid as colorless crystals.

Yield: 70%
m.p.: 85° to 87° C.

(2) A mixture of 5.0 g of this product, 20 ml of toluene, and 200 mg of p-toluenesulfonic acid was refluxed for 4 hours. After cooling, a saturated aqueous sodium hydrogen carbonate solution was added, the mixture was extracted with ethyl acetate, washed with water and dried, followed by evaporation of the solvent. Recrystallization of the residue from ethyl acetate gave 1.24 g of 5-(4-chlorophenyl)-δ-valerolactone as colorless prisms.

m.p.: 110° to 111° C.

(3) A mixture of 200 mg of 5-(4-chlorophenyl)-δ-valerolactone, 0.5 g of aniline, 20 mg of p-toluenesulfonic acid and 10 ml of xylene was refluxed for 6 hours. After removal of solvent, the residue was extracted with ethyl acetate. The extract was washed with diluted hydrochloric acid and a saturated aqueous sodium chloride solution and dried. After removal of the solvent, the residue was purified, by silica gel thin layer chromatography (solvent; chloroform:methanol=10:1) to give 60 mg of 6-(4-chlorophenyl)-1-phenyl-2-piperidone.

M.p., IR, Mass and NMR spectra of this product were identical with those of the compound obtained in Example 1-(2).

Example 37

To 20 g of 4-phenyl-γ-butyrolactone were added 28 g of aniline and 7.6 g of aniline hydrochloride, and the mixture was heated with stirring at 180° C. for 5 hours while evaporating the water formed. After cooling, 200 ml of benzene was added, and the mixture was washed with 10% hydrochloric acid and a saturated aqueous sodium chloride solution and dried. After removal of the solvent, the residue was recrystallized from ethyl acetate to give 24.9 g of 1,5-diphenyl-2-pyrrolidone.

Yield: 85.0% m.p.: 106° to 108° C.
IR $\nu_{max}^{nujol}$(cm$^{-1}$): 1705
Mass (m/e): 237 (M$^+$)

Example 38

4-(Methoxyphenyl)-γ-butyrolactone and p-anisidine were treated in the same manner as in Example 37 to give 1,5-bis(4-methoxyphenyl)-2-pyrrolidone.

Yield: 77%
m.p.: 91.5° to 92.5° C.
IR $\nu_{max}^{nujol}$(cm$^{-1}$): 1690
Mass (m/e): 297 (M$^+$)

Example 39

4-(Chlorophenyl)-γ-butyrolactone and aniline were treated in the same manner as in Example 37 to give 5-(4-chlorophenyl)-1-phenyl-2-pyrrolidone.

M.p., IR, Mass and NMR spectra of this product were identical with those of the compound obtained in Example 35.

Example 40

(1) To 5.4 g of 4-phenyl-γ-butyrolactone were added 11.9 g of ethyl p-aminophenylacetate and 2.7 g of ethyl p-aminophenylacetate hydrochloride, and the mixture was heated with stirring at 180° C. for 35 minutes. After cooling, ethyl acetate was added, and the mixture was washed with 10% hydrochloric acid, an saturated aqueous sodium chloride solution and dried, followed by evaporation of the solvent. The residue was purified by silica gel column chromatography (solvent; benzene:ethyl acetate=10:1) to give 1.5 g of ethyl 4-(2-oxo-5-phenylpyrrolidine)phenylacetate.

m.p.: 82.0° to 84.0° C.

(2) To 0.97 g of this product were added 3.3. ml of a 1N aqueous sodium hydroxide solution and 30 ml of dioxane, and the mixture was stirred at room temperature for 50 minutes. The mixture was adjusted to pH 7 with diluted hydrochloric acid and then the solvent was evaporated. The residue was extracted with ethyl acetate, and the extracts were washed with 10% hydrochloric acid and a saturated aqueous sodium chloride solution and dried. After removal of the solvent, the residue was recrystallized from ethyl acetate to give 0.71 g of 4-(2-oxo-5-phenylpyrrolidine)phenylacetic acid.

Yield: 89%
m.p.: 187° to 190.5° C.
IR $\nu_{max}^{nujol}$(cm$^{-1}$): 1730, 1640
Mass (m/e): 295 (M$^+$)

Examples 41 to 43

Corresponding starting compounds were treated in the same manner as in Example 40 to give the compounds as listed below in Table 3.

TABLE 3

$$\underset{\text{(IV)}}{\overset{O\text{---}C=Z}{\underset{R^1\text{---}CH\text{---}(CH_2)_n}{|\quad\quad|}}} \xrightarrow[\text{(+ additional hydrolysis)}]{+R^2NH_2} \underset{\text{(I)}}{\overset{R^2\text{---}N\text{---}C=Z}{\underset{R^1\text{---}CH\text{---}(CH_2)_n}{|\quad\quad|}}}$$

(Z = O, n = 2)

| Example No. | Compound (I) R$^1$ | Compound (I) R$^2$ | Physical property m.p. (°C.) (solvent for recrystallization), IR | Yield (%) |
|---|---|---|---|---|
| 41 |  |  CH$_2$COOH | 140–142.5 (ethyl acetate) IR$\nu_{max}^{nujol}$ (cm$^{-1}$): 1720, 1660 | — |
| 42 |  |  COOH | 198–206.5 (benzene-isopropyl ether) IR$\nu_{max}^{nujol}$ (cm$^{-1}$): 1710, 1640 | — |
| 43 |  | COOH, OH (on phenyl) | 238–240 (ethyl acetate-isopropyl ether) IR$\nu_{max}^{nujol}$ (cm$^{-1}$): 1670, 1640 | — |

Example 44

(1) To 4.44 g of 4-(4-methoxybenzoyl)butanoic acid was added a solution of 0.8 g of sodium hydroxide in 30 ml of water, and to this solution was added 1.5 g of sodium borohydride, followed by stirring of the mixture at room temperature for 24 hours. The mixture was neutralized with diluted hydrochloric acid, extracted with ether, washed with water and dried, followed by evaporation of the solvent to give 4.4 g of 5-hydroxy-5-(4-methoxyphenyl)pentanoic acid as yellow oily product.

(2) To this product were added 2.2. g of triethylamine and 100 ml of tetrahydrofuran, and after cooling to −10° C., a solution of 3.0 g of isobutyl chlorocarbonate in 10 ml of tetrahydrofuran were added, followed by stirring at −10° C. for 15 minutes and then at room temperature for 40 minutes. After removal of the solvent, the residue was extracted with ether. The ether extract was washed with water and dried. After removal of the solvent, the residue was recrystallized from isopropyl ether to give 3.6 g of 5-(4-methoxyphenyl)-δ-valerolactone as colorless crystals.

Yield: 87%
m.p.: 57.5° to 59.5° C.

(3) A mixture of 6.42 g of this product, 15 ml of aniline and 100 mg of p-toluenesulfonic acid was heated with stirring at 125° C. for 4 hours. The reaction mixture was extracted with ethyl acetate, and the extract was washed with diluted hydrochloric acid and a saturated aqueous sodium chloride solution and dried. After removal of the solvent, the residue was recrystallized from a mixture of ethyl acetate and n-hexane to give 6.25 g of 5-hydroxy-5-(4-methoxyphenyl)-N-phenylpentaneamide.

Yield: 67%
m.p.: 96° to 96.5° C.

(4) To a solution of 0.6 g of this product in 5 ml of methylene chloride was added 0.6 g of triethylamine and to the mixture, under cooling, a solution of 0.46 g of methane sulfonylchloride in 5 ml of methylene chloride was added, and the mixture was stirred at room temperature for 1 hour. The methylene chloride solution was washed with water and dried, followed by evaporation of the solvent. The residue was purified by silica gel column chromtography (solvent; chloroform:methanol=40:1) and recrystallized from a mixture of ethyl acetate and isopropyl ether to give 0.35 g of 6-(4-methoxyphenyl)-1-phenyl-2-piperidone.
Yield: 63%
m.p.: 77° to 78° C.
IR $\nu_{max}^{nujol}(cm^{-1})$: 1650
Mass (m/e): 281 (M+)

Example 45

(1) A mixture of 24.7 g of 5-(4-methoxphenyl)-δ-valerolactone, 50 g of p-anisidine, and 500 mg of p-toluenesulfonic acid was heated with stirring at 125° C. for 4.5 hours. Ethyl acetate was added to the reaction mixture and the precipitated crystals were filtered. The filtrate was washed with diluted hydrochloric acid and water and after drying the solvent was evaporated. The crystals were combined with the previously filtered crystals and the mixture was recrystallized from ethyl acetate to give 33.9 g of 5-hydroxy-5-(4-methoxyphenyl)-N-(4-methoxyphenyl)pentaneamide.
Yield: 86%
m.p.: 118° to 119.5° C.

(2) To a solution of 32.9 g of this product in 300 ml of methylene chloride was added 30.3 g of triethylamine and to the mixture, under cooling, 22.9 g of methane sulfonylchloride was added, and the mixture was stirred at room temperature for 1 hour and at 30° to 40° C. for 30 minutes. The reaction mixture was made acidic with diluted hydrochloric acid. The methylene chloride layer was washed with water and dried, followed by evaporation of the solvent. Recrystallization of the residue from ethyl acetate gave 9.45 g of 1,6-bis(4-methoxyphenyl)-2-piperidone as pale yellow prisms.
m.p.: 108° to 109° C.
IR $\nu_{max}^{nujol}(cm^{-1})$: 1650
Mass (m/e): 311 (M+)

Example 46

(1) To 1.94 g of 5-hydroxy-5-phenylpentanoic acid were added 0.5 ml of pyridine and 5 ml of thionyl chloride, and the mixture was stirred at 70° to 80° C. for 7 hours. Excessive thionyl chloride was distilled off under reduced pressure, and the residue was dissolved in 10 ml of benzene. To this solution was added a solution of 1.86 g of aniline and 1.20 g of pyridine in 10 ml of benzene under cooling and with stirring. After stirring at room temperature for 30 minutes, 50 ml of ethyl acetate was added, and the mixture was washed with diluted hydrochloric acid and a saturated aqueous sodium chloride solution and dried, followed by evaporation of the solvent, to give 3.33 g of crude 5-chloro-5-phenyl-N-phenylpentaneamide as yellow oily product.

(2) A solution of this product in 10 ml of ethanol was added to a sodium alcoholate solution prepared from 0.35 g of metallic sodium and 15 ml of ethanol, and the mixture was refluxed for 50 minutes. The solvent was evaporated and the residue was extracted with ethyl acetate. The ethyl acetate extract was washed with water and dried, followed by evapoaration of the solvent. Recrystallization of the residue from a mixture of ethyl acetate and n-hexane gave 1.29 g of 1,6-diphenyl-2-piperidone as pale yellow prisms.
Yield: 52%
m.p.: 123° to 125° C.
IR $\nu_{max}^{nujol}(cm^{-1})$: 1640
Mass (m/e): 251 (M+)

Examples 47 to 49

Corresponding starting compounds were treated in the same manner as in Example 46 to give the compounds as listed below in Table 4.

TABLE 4

$$\begin{array}{c} R^1 \quad\quad Z \\ | \quad\quad || \\ HO-CH-(CH_2)_n-C-OH \end{array} \longrightarrow \begin{array}{c} R^2-N-C=Z \\ | \quad\quad | \\ R^1-CH-(CH_2)_n \end{array}$$

(IX) → (I)

(Z = O, n = 3)

| Example No. | Compound (I) R¹ | R² | Physical property m.p. (°C.) (solvent for recrystallization), IR | Yield (%) |
|---|---|---|---|---|
| 47 | —⟨phenyl⟩ | —⟨phenyl⟩—Cl | 121–123 (benzene-n-hexane) IR$\nu_{max}^{nujol}$ (cm$^{-1}$): 1640 | 61 |
| 48 | —⟨phenyl⟩—Cl | —⟨phenyl⟩ | identical with the title compound obtained in Example 1 | — |
| 49 | —⟨phenyl⟩ | —⟨phenyl⟩—OCH₃ | 94–96 (carbon tetrachloride) IR$\nu_{max}^{nujol}$ (cm$^{-1}$): 1645 | — |

Example 50

(1) to 6.34 g of 5-(4-chlorophenyl)-5-hydroxypentanoic acid were added 25 ml of thionyl chloride and 0.3 ml of pyridine, and the mixture was stirred at 70° to 80° C. for 2 hours. After removal of the solvent under reduced pressure, the residue was dissolved in 15 ml of methylene chloride. This solution was added dropwise under cooling into a solution of 2.74 g of 3-aminopyridine in 30 ml of methylene chloride and 4.5 ml of pyridine, and the mixture was allowed to room temperature and stirred for 13 hours. A saturated aqueous sodium hydrogen carbonate solution was added to the reaction mixture. The methylene chloride layer was washed with water and dried, followed by evaporation of the solvent to give 9.24 g of 5-chloro-5-phenyl-N-(3-pyridyl)pentaneamide.

(2) A solution of this product in 100 ml of tetrahydrofuran was added portionwise into a solution of 10.56 g of 63% sodium hydride in 30 ml of tetrahydrofuran, and further 1.3 g of potassium iodide and 100 mg of 1,4,7,10,13,16-hexaoxycylooctadecane were added and the mixture was refluxed for 2 hours. After cooling, the reaction mixture was diluted with water and adjusted to pH 8 with diluted hydrochloric acid, extracted with ethyl acetate. The ethyl acetate extracts were washed with water and dried, followed by evaporation of the solvent. The residue was purified by silica gel column chromatography (solvent; chloroform:methanol=30:1) and recrystallized from ethyl acetate to give 1.48 g of 6-(4-chlorophenyl)-1-(3-pyridyl)-2-piperidone as colorless crystals.

m.p.: 107° to 108° C.

IR $\nu_{max}^{nujol}$(cm$^{-1}$): 1640

Mass (m/e: 286 (M+)

Hydrochloride: yellow oily product

IR $\nu_{max}^{neat\ (cm-1)}$: 1635

Mass (m/e): 286 (M+)

Example 51

(1) To 14.7 g of 5-(4-chlorophenyl)-5-hydroxypentanoic acid were added 30 ml of thionyl chloride and 0.5 ml of pyridine at 0° to 10° C. with stirring, and the mixture was heated at 73° C. for 8 hours. After removal of excess thionyl chloride under reduced pressure, 20 ml of benzene was added and again evaporated under reduced pressure. The residue was dissolved in 20 ml of benzene, and this solution was added into a solution of 8.4 g of aniline and 9.5 g of pyridine in 50 ml of benzene under cooling at 0° to 10° C. over 30 minutes. After stirring at room temperature for 50 minutes, 50 ml of benzene was added and the mixture was washed with 10% hydrochloric acid, a saturated aqueous sodium hydrogencarbonate solution and a saturated aqueous sodium chloride solution and dried. After removal of the solvent, the residue was recrystallized from a mixture of benzene and n-hexane to give 12.0 g of 5-chloro-5-(4-chlorophenyl)-N-phenylpentaneamide as pale red powder.

Yield: 58.2% m.p.: 99° to 102° C.

(2) To a solution of 12 g of this product in 50 ml of ethanol, 40 ml of ethanol containing 5.03 g of sodium ethoxide was added. The mixture was refluxed for 5 hours, and then the solvent was evaporated. The residue was purified by silica gel column chromatography (solvent; ethyl acetate:n-hexane=5:1) to give 7.1 g of 6-(4-chlorophenyl)-1-phenyl-2-piperidone as colorless prisms.

Yield: 67%

M.p., IR, Mass and NMR spectra of this product were identical with those of the compound obtained in Example 1-(2).

Example 52

To a solution of 4.27 g of 6-(4-chlorophenyl)-1-phenyl-2-piperidone in 50 ml of dimethoxyethane was added 4.26 g of 2,4-bis(4-methoxyphenyl)-1,3-dithia-2,4-diphosphetane-2,4-disulfide, and the mixture was stirred at room temperature for 2 hours and then refluxed for 1 hour. After removal of the solvent under reduced pressure, the residue was diluted with an aqueous sodium hydrogencarbonate solution, extracted with ethyl acetate, washed with a saturated aqueous sodium chloride solution and dried. After removal of the solvent, the residue was purified by silica gel column chromatography (solvent; ethyl acetate:n-hexane=3:1 and chloroform:n-hexane=2:1, developed twice) and recrystallized from a mixture of ethyl acetate-isopropyl ether-n-hexane to give 3.59 g of 6-(4-chlorophenyl)-1-phenyl-2-thiopiperidone as colorless prisms.

Yield: 80% m.p.: 129.5° to 130.0° C.

IR $\nu_{max}^{nujol}$(cm$^{-1}$): 1595

Mass (m/e): 301 (M+)

Example 53

To a stirred mixture of 2.95 g of 6-(4-chlorophenyl)-1-(4-methoxyphenyl)-2-piperidone, 3 ml of ethanethiol, and 50 ml of methylene chloride was added, under ice-cooling 5.06 g of anhydrous aluminum chloride. After stirring at room temperature for 1 hour, the mixture was poured into ice-cold water and extracted with chloroform. The extract was washed with an aqueous sodium hydrogen carbonate solution and a saturated aqueous sodium chloride solution, dried, and concentrated. The residue was recrystallized from a mixture of ethyl acetate and n-hexane to give 2.75 g of 6-(4-chlorophenyl)-1-(4-hydroxyphenyl)-2-piperidone as colorless needles.

Yield: 97% m.p.: 209° to 210° C.

IR $\nu_{max}^{nujol}$(cm$^{-1}$): 1620

Mass (m/e): 301 (M+)

Examples 54 to 56

The products obtained in Examples 15, 21 and 23 were treated in the same manner as in Example 53 to give the compounds as listed below in Table 5.

TABLE 5

$$R^2\text{—}N\text{——}C\text{=}Z \qquad (I)$$
$$R^1\text{—}CH\text{—}(CH_2)_n$$
$$(Z = O, n = 3)$$

| Example No. | Compound (I) R¹ | R² | Physical property m.p. (°C.) (solvent for recrystallization), IR | Yield (%) |
|---|---|---|---|---|
| 54 | 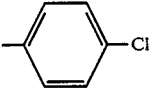 | 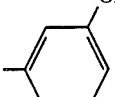 | 158.5–159 (ethyl acetate-isopropyl ether) IR$\nu_{max}^{nujol}$ (cm$^{-1}$): 1620 | 92 |
| 55 | 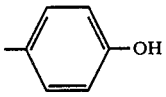 | 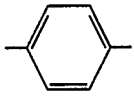 | 205.5–206.5 (ethanol-n-hexane) IR$\nu_{max}^{nujol}$ (cm$^{-1}$): 3250, 1625 | 92 |
| 56 | 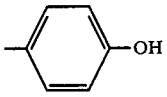 | 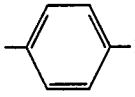 | 176.5–177.5 (ethanol ethyl acetate-n-hexane) IR$\nu_{max}^{nujol}$ (cm$^{-1}$): 3250, 1630, 1610 | 93 |

Example 57

To a solution of 670 mg of 6-(3,4-dimethoxyphenyl)-1-(4-chlorophenyl)-2-piperidone in 17 ml of methylene chloride was added, under ice-cooling, 1.0 ml of boron tribromide, and the mixture was stirred under ice-cooling for 1 hour and at room temperature for 45 minutes. The mixture was treated with ice-water, extracted with chloroform. The extracts were washed with water, dried, and concentrated under reduced pressure. The residue was recrystallized from ethyl acetate to give 480 mg of 6-(3,4-dihydroxyphenyl)-1-(4-chlorophenyl)-2-piperidone as colorless prisms.

Yield: 78%
m.p.: 205° to 207° C.
IR $\nu_{max}^{nujol}$(cm$^{-1}$): 3450, 1625, 1610
Mass (m/e): 317 (M$^+$)

Example 58

A mixture of 2.32 g of 6-(4-chlorophenyl)-1-(4-fluorophenyl)-2-piperidone, 25 ml of dimethylformamide, 5 ml of formic acid, and 1.0 g of palladium-carbon was refluxed for 6 hours. The catalyst was filtered off, and the filtrate was extracted with ethyl acetate. The ethyl acetate solution was washed with water and an aqueous sodium hydrogen carbonate solution and dried. After removal of the solvent, the residue was recrystallized from a mixture of isopropyl ether and n-hexane to give 1.25 g of 1-(4-fluorophenyl)-6-phenyl-2-piperidone as colorless prisms.

Yield: 61%
m.p.: 87.5° to 88.5° C.
IR $\nu_{max}^{nujol}$(cm$^{-1}$): 1650, 1600
Mass (m/e): 269 (M$^+$)

Examples 59 to 64

The products obtained in Examples 6, 8, 15, 27, 53 and 54 were treated in the same manner as in Example 58 to give the corresponding piperidones as listed below in Table 6.

TABLE 6

$$R^2\text{—}N\text{——}C\text{=}Z \qquad (I)$$
$$R^1\text{—}CH\text{—}(CH_2)_n$$
$$(Z = O, n = 3)$$

| Example No. | Compound (I) R¹ | R² | Physical property m.p. (°C.) (solvent for recrystallization) IR | Yield (%) |
|---|---|---|---|---|
| 59 |  |  | 121.5–122.5 (isopropyl ether) IR$\nu_{max}^{nujol}$ (cm$^{-1}$): 1640 | 86 |
| 60 |  |  | 143.5–144.5 (isopropyl ether) IR$\nu_{max}^{nujol}$ (cm$^{-1}$): 1640 | 87 |
| 61 |  |  | 95.5–98 (isopropyl ether) IR$\nu_{max}^{nujol}$ (cm$^{-1}$): 1640 | 82 |
| 62 |  |  | 196.5–198 (ethyl acetate-ethanol-n-hexane) IR$\nu_{max}^{nujol}$ (cm$^{-1}$): 1600 | 65 |
| 63 |  |  | 198–200 (ethyl acetate-ethanol-n-hexane) IR$\nu_{max}^{nujol}$ (cm$^{-1}$): 1620 | 64 |
| 64 |  | 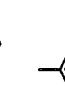 | 105–106 (isopropyl ether-n-hexane) IR$\nu_{max}^{nujol}$ (cm$^{-1}$): 1640 | 68 |

Example 65

To 8.55 g of 6-(4-chlorophenyl)-1-phenyl-2-piperidone were added 5.58 g of copper cyanide and 14 ml of pyridine, and the mixture was heated with stirring at 240° C. for 19 hours. The mixture was treated with diluted ammonia water, and then extracted with ethyl acetate. The extracts were washed with water, dried and treated with activated charcoal. After removal of charcoal and the solvent, the residue was purified by silica gel column chromatography (solvent; ethyl acetate:n-hexane=1:1 to 3), and recrystallized from a mixture of ethyl acetate and isopropyl ether to give 3.48 g of 6-(4-cyanophenyl)-1-phenyl-2-piperidone as pale yellow prisms.

Yield: 47%
m.p.: 119.5° to 120° C.
IR $\nu_{max}^{nujol}$(cm$^{-1}$): 2235, 1650
Mass (m/e): 276 (M$^+$)

Example 66

To a stirred mixture of 7.7 g of 1-(4-chlorophenyl)-6-(4-methylthiophenyl)-2-piperidone, 80 ml of methylene chloride, 3 g of silica gel, and 2.2 g of water was added 3.44 g of sulfuryl chloride at 15° to 25° C., and the mixture was stirred at 15° to 25° C. for 2 hours. The reaction mixture was poured into a cold aqueous sodium hydrogen carbonate solution. The methylene chloride solution was washed with a saturated aqueous sodium chloride solution, dried, and concentrated. The residue was purified by silica gel column chromatography (solvent; ethyl acetate:ethanol=10:1) and recrystallization from ethyl acetate to give 7.69 g of 1-(4-chlorophenyl)-6-(4-methylsulfinylphenyl)-2-piperidone as colorless prisms.

Yield: 95.2%
m.p.: 142° to 165° C.
IR $\nu_{max}^{nujol}$(cm$^{-1}$): 1650, 1040
Mass (m/e): 347 (M$^+$)

Example 67

To a solution of 1.70 g of 1-(4-chlorophenyl)-6-(4-methylsulfinylphenyl)-2-piperidone in 50 ml of methylene chloride was added 1.02 g of m-chloroperbenzoic acid with stirring at 5° to 10° C. over 30 minutes. After stirring at 5° to 10° C. for 1 hour and at room temperature for 1 hour, the mixture was made alkaline with a saturated aqueous sodium hydrogen carbonate solution. The methylene chloride layer was washed with water, dried, and concentrated. The residue was recrystallized from nitroethane to give 1.54 g of 1-(4-chlorophenyl)-6-(4-methylsulfonylphenyl)-2-piperidone as colorless prisms.

Yield: 88.5%
m.p.: 231° to 232° C.
IR $\nu_{max}^{nujol}$(cm$^{-1}$): 1640, 1305, 1160, 1140
Mass (m/e): 363 (M$^+$)

Example 68

To a solution of 2.5 g of 1-(4-chlorophenyl)-6-(4-methylsulfonylphenyl)-2-piperidone in 10 ml of methylene chloride, 15 ml of anhydrous trifluoroacetic acid was added, and the mixture was refluxed at 45° C. for 3 hours. After cooling, 100 ml of a mixture of methanol and triethylamine (1:1) was added, and the mixture was stirred at room temperature for 1 hour and then treated with a saturated aqueous ammonium chloride solution. The methylene chloride layer was washed with water, dried, and evaporated to give 2.2 g of 1-(4-chlorophenyl)-6-(4-mercaptophenyl)-2-piperidone as pale yellow oily product.

Yield: 96.5%
IR $\nu_{max}^{nujol}$(cm$^{-1}$): 3400, 1640
Mass (m/e): 317 (M$^+$)

Example 69

A solution of 6.5 g of 1-(4-nitrophenyl)-6-(3,4-dichlorophenyl)-2-piperidone in 180 ml of methanol was cooled to 4° C., and then 110 g of 25% titanium trichloride was added dropwise to the solution. After stirring at 18° to 20° C. for 40 minutes, the reaction mixture was poured into cold ammonia water and the precipitates were filtered off. The filtrate was extracted with chloroform. On the other hand, the precipitate obtained above was throughly washed with chloroform. The chloroform layer was combined with the former, washed with water, dried, and concentrated. The residue was recrystallized from ethanol to give 4.59 g of 1-(4-aminophenyl)-6-(3,4-dichlorophenyl)-2-piperidone as colorless prisms.

Yield: 77%
m.p.: 177° to 178° C.
IR $\nu_{max}^{nujol}$(cm$^{-1}$): 3440, 3340, 1620, 1600
Mass (m/e): 335 (M$^+$)

Example 70

1-(3-Nitrophenyl)-6-(3,4-dichlorophenyl)-2-piperidone was treated in the same manner as in Example 69 to give 1-(3-aminophenyl)-6-(3,4-dichlorophenyl)-2-piperidone.

Yield: 75%
m.p.: 202° to 203° C. (recrystallized from ethanol)
IR $\nu_{max}^{nujol}$(cm$^{-1}$): 3430–3240, 1650, 1610
Mass (m/e): 335 (M$^+$)

Example 71

To a solution of 2.42 g of 1-(4-aminophenyl)-6-(3,4-dichlorophenyl)-2-piperidone in 20 ml of chloroform were added 5 ml of acetic anhydride and 0.5 ml of pyridine, and the mixture was stirred at room temperature for 30 minutes and then at 80° C. for 30 minutes. The reaction mixture was cooled and diluted with isopropyl ether. The crystals precipitated were filtered and recrystallized from a mixture of ethanol and dimethylformamide to give 2.69 g of 1-(4-acetylaminophenyl)-6-(3,4-dichlorophenyl)-2-piperidone as colorless prisms.

Yield: 99%
m.p.: 267° to 268° C.
IR $\nu_{max}^{nujol}$(cm$^{-1}$): 3310, 3270, 1690, 1620, 1600
Mass (m/e): 377 (M$^+$)

Example 72

To 1.00 g of 1-(4-chlorophenyl)-6-(4-hydroxyphenyl)-2-piperidone was added 25 ml of acetic anhydride and the mixture was stirred at 120° C. for 1 hour. The solvent was evaporated under reduced pressure and the residue was recrystallized from ethyl acetate to give 910 mg of 1-(4-chlorophenyl)-6-(4-acetoxyphenyl)-2-piperidone as colorless prisms.

Yield: 80%
m.p.: 196° to 197° C.
IR $\nu_{max}^{nujol}$(cm$^{-1}$): 1745, 1640
Mass (m/e): 343 (M$^+$)

Example 73

To 0.25 g of 1,6-diphenyl-2-piperidone were added 0.30 g of phosphorus pentachloride, 0.5 ml of sulfuryl chloride and 5 ml of chloroform, and the mixture was refluxed for 1.5 hours. The reaction mixture was concentrated under reduced pressure, made alkaline with an aqueous sodium hydrogen carbonate solution, and extracted with 30 ml of ethyl acetate. The ethyl acetate extract was washed with water, dried, and concentrated to give 0.21 g of 1-(4-chlorophenyl)-6-phenyl-2-piperidone.

M.p. and IR spectra of this product were identical with those of the compound obtained in Example 47.

Example 74

To a solution of 1.0 g of 1-phenyl-6-(3,4-dichlorophenyl)-2-piperidone in 0.5 ml of acetic anhydride was added 1 ml of fuming nitric acid at 0° to 10° C., and the mixture was stirred for 3 hours. The mixture was made alkaline under cooling with an aqueous 10% sodium hydroxide solution and extracted with toluene. After washing with water and drying, the solvent was evaporated. The residue was purified by silica gel column chromatography (solvent; acetone:n-hexane=1:1) to give 0.35 g of 1-(4-nitrophenyl)-6-(3,4-dichlorophenyl)-2-piperidone as colorless foam.

IR spectrum of this product was identical with that of the compound obtained in Example 32.

What is claimed is:

1. A lactam of the formula:

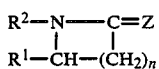

wherein

R$^1$ is a phenyl group or a phenyl group having 1 or 2 substituents selected from a halogen atom, a lower alkoxy group, a lower alkyl group, hydroxy group, a lower alkylthio group, a thiol group, cyano group, a lower alkanoyloxy group, a lower alkylsulfinyl group, a lower alkylsulfonyl group, a trihalogeno-lower alkyl group, nitro group, amino group, a lower alkanoylamino group, carboxyl group and a carboxy-lower alkyl group;

R$^2$ is a phenyl group or a phenyl group having 1 to 2 substituents selected from a halogen atom, a lower alkoxy group, a lower alkyl group, hydroxy group, a lower alkylthio group, thiol group, cyano group, a lower alkonoyloxy group, a lower alkylsulfinyl group, a lower alkylsulfonyl group, a trihalogeno-lower alkyl group, nitro group, amino group, a lower alkanoylamino group, carboxyl group and a carboxy-lower alkyl group; a cycloalkyl group of 3 to 7 carbon atoms, pyridyl group, pyrazinyl group, pyrimidyl group or pyridazinyl group;

Z is a oxygen atom or sulfur atom; and n is 2 or 3.

2. The compound claimed in claim 1, in which R$^1$ is phenyl group or a phenyl group having 1 to 2 substituent(s) selected from a halogen atom, a lower alkyl group, a lower alkylthio group, hydroxy group and a lower alkoxy group; R$^2$ is phenyl group, a phenyl group having 1 to 2 substituent(s) selected from a halogen atom, a lower alkoxy group, a lower alkyl group, a lower alkanoylamino group, hydroxy group, nitro group and amino group, or a cycloalkyl group of 3 to 7 carbon atoms; Z is oxygen atom; and n is 3.

3. The compound claimed in claim 2, in which R$^1$ is phenyl group or a phenyl group having 1 to 2 substituent(s) selected from a halogen atom, an alkyl group of 1 to 3 carbon atoms, an alkylthio group of 1 to 3 carbon atoms, hydroxy group and an alkoxy group of 1 to 3 carbon atoms; and R$^2$ is phenyl group, a phenyl group having 1 to 2 substituent(s) selected from a halogen atom, an alkoxy group of 1 to 3 carbon atoms, an alkyl group of 1 to 3 carbon atoms, an alkanoylamino group of 1 to 3 carbon atoms, hydroxy group, nitro group and amino group, or a cycloalkyl group of 4 to 7 carbon atoms.

4. The compound claimed in claim 3, in which R$^1$ is phenyl group or a phenyl group having 1 to 2 susbstituent(s) selected from a halogen atom, an alkyl group of 1 to 3 carbon atoms and an alkoxy group of 1 to 3 carbon atoms; and R$^2$ is phenyl group, a phenyl group having 1 to 2 substituent(s) selected from a halogen atom, an alkoxy group of 1 to 3 carbon atoms, an alkyl group of 1 to 3 carbon atoms, nitro group and amino group, or a cycloalkyl group of 4 to 7 carbon atoms.

5. The compound claimed in claim 4, in which R$^1$ is a phenyl group having 1 or 2 substituent(s) selected from a halogen atom; and R$^2$ is phenyl group, a phenyl group having a substituent selected from a halogen atom, an alkoxy group of 1 to 3 carbon atoms, an alkyl group of 1 to 3 carbon atoms, nitro group and an amino group, or a cycloalkyl group of 4 to 7 carbon atoms.

6. The compound claimed in claim 5, in which R$^1$ is a phenyl group having 1 or 2 substituent(s) selected from fluorine atom, chlorine atom, bromine atom and iodine atom; and R$^2$ is phenyl group, a phenyl group having a substituent selected from fluorine atom, chlorine atom, methoxy group, methyl group, nitro group and amino group, or cyclohexyl group.

7. The compound claimed in claim 6, in which R$^1$ is 4-fluorophenyl group, 4-chlorophenyl group, 4-bromophenyl group, 4-iodophenyl group, 3-chlorophenyl group or 3,4-dichlorophenyl group; and R$^2$ is phenyl group, 3-fluorophenyl group, 3-chlorophenyl group, 3-methoxyphenyl group, 4-methoxyphenyl group, 4-fluorophenyl group, 3-nitrophenyl group, 4-aminophenyl group, 3-aminophenyl group or cyclohexyl group.

8. An acid addition salt of the compound of claim 1 in which R$^1$ is a lower alkanoylamino phenyl group or an aminophenyl group and R$^2$ is a lower alkanoylaminophenyl group, an aminophenyl group, a pyridyl group, a pyrazinyl group a pyrimidyl group, or pyridazinyl group.

9. An acid addition salt of the compound of claim 3 in which R$^2$ is a lower alkanoylaminophenyl group or an aminophenyl group.

10. An acid addition salt of the compound of any of claims 4, 5 or 6 in which R$^2$ is an aminophenyl group.

11. An acid addition salt of the compound of claim 8 in which R$^2$ is 3- or 4-aminophenyl group.

12. The compound claimed in claim 7, which is selected from:
6-(4-chlorophenyl)-1-(3-chlorophenyl)-2-piperidone,
6-(4-chlorophenyl)-1-(3-fluorophenyl)-2-piperidone,
6-(4-chlorophenyl)-1-(4-methylphenyl)-2-piperidone,
6-(4-fluorophenyl)-1-phenyl-2-piperidone,
6-(4-chlorophenyl)-1-(3-methoxyphenyl)-2-piperidone,
6-(3-chlorophenyl)-1-phenyl-2-piperidone,
6-(4-chlorophenyl)-1-phenyl-2-piperidone, 6-(3,4-dichlorophenyl)-1-phenyl-2-piperidone,
6-(3,4-dichlorophenyl)-1-(4-aminophenyl)-2-piperidone and 6-(3,4-dichlorophenyl)-1-(3-aminophenyl)-2-piperidone.

13. An acid addition salt of the compound of claim 12, which is selected from 6-(3,4-dichlorophenyl)-1-(4-aminophenyl)-2-piperidone and 6-(3,4-dichlorophenyl)-1-(3-aminophenyl)-2-piperidone.

14. The compound claimed in claim 12, which is 6-(4-chlorophenyl)-1-phenyl-2-piperidone.

15. A pharmaceutical composition for the therapeutic treatment of or amelioration of central dopaminergic system disorders which comprises a therapeutically effective amount of a compound claimed in claim 1 and a pharmaceutically acceptable carrier therefor.

16. A pharmaceutical composition for the therapeutic treatment of or amelioration of central system disorders which comprises a therapeutically effective amount of the compound claimed in claim 3 and a pharmaceutically acceptable carrier therefor.

17. A pharmaceutical composition for the therapeutic treatment or amerlioration of central dopaminergic system disorders which comprises a therapeutically effective amount of the compound claimed in claim 6 and a pharmaceutically acceptable carrier therefor.

18. A pharmaceutical composition for the therapeutic treatment or amelioration of central dopaminergic system disorders which comprises a therapeutically effective amount of the compound claimed in claim 12 and a pharmaceutically acceptable carrier therefor.

19. A pharmaceutical composition for the therapeutic treatment or amelioration of central dopaminergic system disorders which comprises a therapeutically effective amount of the compound claimed in claim 14 and a pharmaceutically acceptable carrier therefor.

20. The pharmaceutical composition claimed in claim 15, in which the central dopaminergic system disorders are
    (1) mental and psychic disorders in senescence,
    (2) depression,
    (3) minimal brain dysfunction in child,
    (4) Parkinson's disease,
    (5) consciousness disorders or
    (6) amnesia.

21. The pharmaceutical composition claimed in claim 16, in which the central dopaminergic system disorders are
    (1) mental and psychic disorders in senescence,
    (2) depression,
    (3) minimal brain dysfunctions in child,
    (4) Parkinson's disease,
    (5) consciousness disorders or
    (6) amnesia.

22. The pharmaceutical composition claimed in claim 18, in which the central dopaminergic system disorders are
    (1) mental and psychic disorders in senescence,
    (2) depression,
    (3) minimal brain dysfunctions in child,
    (4) Parkinson's disease,
    (5) consciousness disorders or
    (6) amnesia.

23. The pharmaceutical composition claimed in claim 18, in which the central dopaminergic system disorders are
    (1) mental and psychic disorders in senescence,
    (2) depression,
    (3) minimal brain dysfunctions in child,
    (4) Parkinson's disease,
    (5) consciousness disorders or
    (6) amnesia.

24. The pharmaceutical composition claimed in claim 20, in which the central dopaminergic system disorders are
    (1) mental and psychic disorders in senescence,
    (2) depression,
    (3) minimal brain dysfunctions in child,
    (4) Parkinson's disease,
    (5) consciousness disorders or
    (6) amnesia.

* * * * *

UNITED STATES PATENT AND TRADEMARK OFFICE
CERTIFICATE OF CORRECTION

PATENT NO. : 4,839,360

DATED : June 13, 1989

INVENTOR(S) : Yasuhiko Sato, et al.

It is certified that error appears in the above-identified patent and that said Letters Patent is hereby corrected as shown below:

Columns 17 & 18:

" 13-(2) 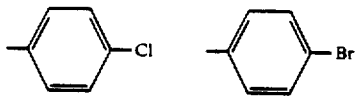 151.5-152.0 66 "
(ethyl acetate-isopropyl ether)
$IR\nu_{max}^{nujol}$
$(cm^{-1}):1640$ 14-(2) 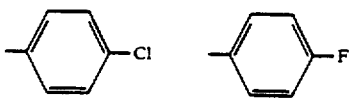 92.5-93.5 90
(ethyl acetate-n-hexane)
$IR\nu_{max}^{nujol}$
$(cm^{-1}):1650$ should read as:

| | | | | |
|---|---|---|---|---|
| 13-(2) | -⟨⟩-Cl | -⟨⟩-Br | 151.5 - 152.0 (ethyl acetate - isopropyl ether) $IR\nu_{max}^{nujol}\ (cm^{-1}):\ 1640$ | 66 |
| 14-(2) | -⟨⟩-Cl | -⟨⟩-F | 100.5 - 101.5 (isopropyl ether - n-hexane) $IR\nu_{max}^{nujol}\ (cm^{-1}):\ 1650$ | 70 |
| 15-(2) | -⟨⟩-Cl | -⟨⟩-OCH$_3$ | 92.5 - 93.5 (ethyl acetate - n-hexane) $IR\nu_{max}^{nujol}\ (cm^{-1}):\ 1650$ | 90 |

UNITED STATES PATENT AND TRADEMARK OFFICE
CERTIFICATE OF CORRECTION

PATENT NO. : 4,839,360

DATED : June 13, 1989

INVENTOR(S) : Yasuhiko Sato, et al.

It is certified that error appears in the above-identified patent and that said Letters Patent is hereby corrected as shown below:

Column 20, after 64, "80" should read as --56--

Column 21, line 57: "Example 24" should read as --Example 34--

Column 22, lines 49-51: "117- (acetic anhydride-isopropyl ether) $IR\nu_{max}^{nujol}$ (cm$^{-1}$):1660, 1610"

should read as --

| 117 - 120 (acetic anhydride -isopropyl ether) $IR\nu_{max}^{nujol}$ (cm$^{-1}$): 1660,1610 | 90 |

--

Signed and Sealed this

Twenty-sixth Day of June, 1990

Attest:

HARRY F. MANBECK, JR.

Attesting Officer

Commissioner of Patents and Trademarks